United States Patent [19]

Kunzler et al.

[11] Patent Number: 5,714,557
[45] Date of Patent: Feb. 3, 1998

[54] MONOMERIC UNITS USEFUL FOR REDUCING THE MODULUS OF LOW WATER POLYMERIC SILICONE COMPOSITIONS

[75] Inventors: Jay F. Kunzler, Canandaigua; Richard M. Ozark, Solvay, both of N.Y.

[73] Assignee: Bausch & Lomb Incorporated, Rochester, N.Y.

[21] Appl. No.: 745,537

[22] Filed: Nov. 12, 1996

Related U.S. Application Data

[60] Provisional application No. 60/088,329, Dec. 7, 1995.

[51] Int. Cl.$^6$ .................................................. C08F 30/08
[52] U.S. Cl. ........................ 526/279; 523/106; 351/160 R
[58] Field of Search ........................ 526/279; 351/160 R; 523/106

[56] References Cited

U.S. PATENT DOCUMENTS

| | | | |
|---|---|---|---|
| 4,153,641 | 5/1979 | Deichert et al. | 260/827 |
| 4,189,546 | 2/1980 | Deichert et al. | 528/26 |
| 4,259,467 | 3/1981 | Keogh et al. | 526/279 |
| 4,709,066 | 11/1987 | Chapman | 556/437 |
| 4,740,533 | 4/1988 | Su et al. | 523/106 |
| 4,810,764 | 3/1989 | Friends et al. | 526/245 |
| 4,824,922 | 4/1989 | Chapman | 526/279 |
| 4,910,277 | 3/1990 | Bambury et al. | 526/260 |
| 4,954,587 | 9/1990 | Mueller | 526/245 |
| 5,010,141 | 4/1991 | Mueller | 525/276 |
| 5,034,461 | 7/1991 | Lai et al. | 525/100 |
| 5,070,215 | 12/1991 | Bambury et al. | 556/418 |
| 5,079,319 | 1/1992 | Mueller | 526/238.23 |
| 5,260,000 | 11/1993 | Nandu et al. | 264/2.1 |
| 5,310,779 | 5/1994 | Lai | 524/588 |
| 5,321,108 | 6/1994 | Kunzler et al. | |
| 5,358,995 | 10/1994 | Lai et al. | 524/547 |
| 5,387,662 | 2/1995 | Kunzler et al. | 526/245 |
| 5,391,589 | 2/1995 | Kiguchi et al. | 523/106 |
| 5,539,016 | 7/1996 | Kunzler et al. | 523/107 |

FOREIGN PATENT DOCUMENTS

0478261A2  4/1992  European Pat. Off. ...... C08F 210/14

OTHER PUBLICATIONS

Doc. No.107:284–30 Kubota et al JP85–178115–850813 in House Computer Generated Abstract pp. 79–83 (19 of 21).
Doc. No. 107:28429–Kubota et al JP85–178114–850813–in House Computer Generated Abstract pp. 83–(Answer 20 0f 21).
Document No. 105:173972–Kubota et al JP84–197462–840920 in House Abstract pp. 85–88 (answer 21 0f 21).
Doc. No. 118:87685 Tetsuo et al JP90–292073–901031 in House Abstract pp. 90–91 (Answer 2 0f 2).
"The Role of Bulky Polysiloxanylalkyl Methacrylates in Polyurethane–Polysiloxane Hydrogels" by Yu–Chin Lai—*Polymeric Materials Science and Engineering*, vol. 72, pp. 118–119.

*Primary Examiner*—Joseph L. Schofer
*Assistant Examiner*—N. Sarofim
*Attorney, Agent, or Firm*—John E. Thomas

[57] ABSTRACT

Monomeric units useful in reducing the modulus of low water polymeric silicone compositions are disclosed. Low water compositions including the subject monomeric units are especially useful in the formation of biomedical articles such as low water silicone contact lenses.

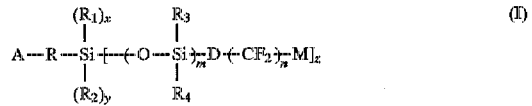

wherein:

A is an activated unsaturated group;

R and D independently are alkyl, alkylene or haloalkyl groups having 1 to 10 carbon atoms wherein said carbon atoms may include ether linkages therebetween;

M is hydrogen, fluorine, or an alkyl group;

$R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;

m is an integer from 1 to 500; n is an integer from 1 to 20; x and y are 0 or 1;

z is 1 or 2; and x+y+z=3;

so long as at least one of $R_1$ or $R_2$ is an alkyl group having from 1 to 10 carbon atoms.

19 Claims, No Drawings

MONOMERIC UNITS USEFUL FOR REDUCING THE MODULUS OF LOW WATER POLYMERIC SILICONE COMPOSITIONS

PRIOR APPLICATIONS

This application claims the benefit of U.S. Provisional Application No. 60/088,329 filed on Dec. 7, 1995.

FIELD OF THE INVENTION

The present invention generally relates to a class of fluorinated siloxane-containing monomeric units and their use in reducing the modulus of low water polymeric silicone compositions. Such materials find particular application in the formulation of contact lenses.

BACKGROUND

Polymeric silicone materials have been used in a variety of biomedical applications, including, for example, the formation of contact lenses. Such materials can generally be subdivided into two major classes, hydrogels and non-hydrogels (referred to herein as "low water" materials). Silicon hydrogels constitute crosslinked polymeric systems that can absorb and retain water in an equilibrium state and generally have a water content greater than about 5 weight percent and more commonly between about 10 to about 80 weight percent. Such materials are usually prepared by polymerizing a mixture containing at least one silicone-containing monomer and at least one hydrophilic monomer. Either the silicone-containing monomer or the hydrophilic monomer may function as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of applicable silicone-containing monomeric units include:

(a) bulky polysiloxanylalkyl (meth)acrylic monomers, commonly referred to as "TRIS" monomers, e.g. methacryloxypropyl tris(trimethylsiloxy)silane;

(b) poly(organosiloxane) monomeric units;

(c) silicone containing monomers includes silicone-containing vinyl carbonate or vinyl carbamate monomers such as; 1,3-bis[4-vinyloxycarbonyloxy)but-1-yl] tetramethyldisiloxane; 3 -(trimethylsilyl)propyl vinyl carbonate; 3-(vinyloxycarbonylthio)propyl-[tris(trimethylsiloxy)silane]; 3-[tris(trimethylsiloxy)silyl] propyl vinyl carbamate;3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate; and (d) poly(organosiloxane) monomeric units including urethane or ureido groups. Other examples of applicable silicone-containing monomers are well known in the art.

Suitable hydrophilic monomers for use in silicone hydrogels include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone; and acrylamides, such as methacrylamide and N,N-dimethylacrylamide. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

In particular regard to the use of silicone hydrogels in the formation of contact lenses, the fluorination of certain monomers has been indicated to reduce the accumulation of deposits on contact lenses, as described in U.S. Pat. Nos. 4,954,587, 5,079,319 and 5,010,141. Moreover, the use of silicone-containing TRIS-type monomers having certain fluorinated side groups, i.e. —($CF_2$)—H, have been found to improve compatibility between the hydrophilic and silicone-containing monomeric units, as described in U.S. Pat. Nos. 5,387,662 and 5,321,108.

Low water silicone materials, like their hydrogel counterparts, include the same class of silicone-containing monomeric units; however, unlike silicone hydrogels, "low water" silicone materials do not include appreciable amounts of hydrophilic monomers and/or internal wetting agents (i.e. typically less than 5 to 10 weight percent). As such, low water silicone materials, as their name suggest, do not absorb or retain appreciable amounts of water, e.g. less than about 5 weight percent, and more typically less than about 1 or 2 weight percent. Examples of low water fluorinated polysiloxanes are disclosed in U.S. Pat. Nos. 4,810,764 and 5,142,009. Such materials are commonly surface treated, e.g. plasma surface treatment, in order to render the surface of the material more hydrophilic. Regardless of surface treatment or the use of hydrophilic monomers and/or internal wetting agents, the total water content of low water silicone compositions is less than about 5 weight percent.

Although low water silicone compositions have very desirable oxygen permeability, they typically possess relatively high moduli (Young's modulus of elasticity), e.g. often in excess of 300 g/mm$^2$ as measured by ASTM test method D1938. For many biomedical applications, it is desirable to provide low water compositions having reduced moduli, e.g. in the range of about 20 g/mm$^2$ to about 150 g/mm$^2$, and more preferably from about 30 g/mm$^2$ to about 100 g/mm$^2$. This is particularly important in the formation of soft contact lenses, as the modulus of lens material can have a significant impact upon lens "comfort." Lenses possessing high moduli often have a perceived stiffness and undesirably high elastic recovery resulting in an unnatural feeling.

Although the use of bulky polysiloxanylalkyl methacrylates, e.g. methacryloxypropyl tris (trimethylsiloxy) silane, commonly referred to as "TRIS", are known to reduce the modulus of some silicone hydrogels, i.e. polyurethane-polysiloxane hydrogel compositions, (see for example; Lai, Yu Chin, *The Role of Bulky Polysiloxanylalkyl Methacrylates in Polyurethane-polysiloxane Hydrogels*, Proceedings of the American Chemical Society Division of Polymeric Materials: Science and Engineering, Vol 72, pg. 118–119, (1995)); the use of TRIS monomeric units within "low water" silicone compositions generally increases the modulus of the resulting material. As such, TRIS monomeric units are not generally helpful in reducing the modulus of low water silicone materials.

U.S. Pat. Nos. 5,321,108 and 5,387,662 disclose a TRIS-type monomeric unit which includes at least one fluoro substituted end group including a terminal hydrogen. This monomeric unit is described as providing increase compatibility as between silicone-containing and hydrophilic monomeric units in the formation of silicone hydrogels. As with TRIS, the described monomeric unit has a bulky polysiloxanylalkyl structure including three (tris) siloxane branches. These TRIS-type fluorinated monomeric units are not distillable through conventional techniques. As such, purification of such materials can be difficult. For this same reason, these materials can also be difficult to analyze, e.g. by use of gas chromatography.

In summary, low water silicone materials are sought which possess relatively low moduli, e.g. from 20 g/mm$^2$ to about 150 g/mm$^2$. Furthermore, in applications such as the formation of contact lenses, such low water materials must be optically clear, manufacturable (e.g., capable of being molded, machined, etc.) have acceptable oxygen permeability, biocompatibility and resist deposit formation. Moreover, low water materials are desired which can be easily sythesized, purified, and analyzed.

SUMMARY OF THE INVENTION

The present invention is a monomeric unit useful for reducing the modulus of low water polymeric silicone materials and is represented by Formula I:

$$A-R-\underset{(R_2)_y}{\overset{(R_1)_x}{Si}}-(-O-\underset{R_4}{\overset{R_3}{Si}})_m-D-(CF_2)_n-M]_z \quad (I)$$

wherein:

A is an activated unsaturated group;

R and D independently are an alkyl, alkylene, or haloalkyl group having 1 to 10 carbon atoms wherein said carbon atoms may include ether linkages therebetween;

M is hydrogen, fluorine, or alkyl group;

$R_1$, $R_2$, $R_3$ and $R_4$ are independently selected from: alkyl or haloalkyl groups wherein ether linkages may be included between carbon atoms; siloxane groups; and aromatic-containing groups having 6 to 18 carbon atoms;

m is an integer equal to 1 or greater; n is an integer from 1 to 20; x and y are 0 or 1;

z is 1 or 2; and x+y+z=3; so long as at least one of $R_1$ or $R_2$ is an alkyl group having from 1 to 10 carbon atoms.

The present invention further includes low water silicone compositions including the subject monomeric units, methods for making such low water silicone compositions, contact lenses made from such compositions, and methods for reducing the moduli of low water silicone compositions.

An advantage of the subject invention is that the monomer units described with reference to Formula I reduce the modulus of low water silicone compositions without significantly reducing the oxygen permeability of the resulting polymeric composition. Furthermore, the subject monomeric units are relatively easy to synthesize, purify, and analyze, and may be polymerized within silicone-containing monomeric units to form low water silicone materials without significantly effecting optical clarity.

DETAILED DESCRIPTION OF THE INVENTION

The present invention relates to monomeric units represented by Formula I (described below), and the use of such monomeric units to reduce the modulus of low water polymeric silicone compositions. Low water silcone compositions of the present invention are formed by polymerizing a monomer mix comprising from about 1 to about 99 weight percent, but more preferably from about 30 to about 60 weight percent of silicone-containing monomeric units, and from about 1 to about 50 weight percent, but preferably from 5 to 30 weight percent of monomeric units represented by Formula I:

$$A-R-\underset{(R_2)_y}{\overset{(R_1)_x}{Si}}-(-O-\underset{R_4}{\overset{R_3}{Si}})_m-D-(CF_2)_n-M]_z \quad (I)$$

wherein:

A is an activated unsaturated group;

R and D independently are an alkyl, alkylene, or haloalkyl group having 1 to 10 carbon atoms wherein said carbon atoms may include ether linkages therebetween;

M is hydrogen, fluorine, or alkyl group but preferably hydrogen or fluorine;

$R_1$, $R_2$, $R_3$ and $R_4$ are independently selected from: alkyl or haloalkyl groups wherein ether linkages may be included between carbon atoms; siloxane groups; and aromatic-containing groups having 6 to 18 carbon atoms (e.g. cycloalkyl groups and aromatic groups such as phenyl groups);

m is an integer equal to 1 or greater; n is an integer from 1 to 20; x and y are 0 or 1;

z is 1 or 2; and x+y+z=3;

so long as at least one of $R_1$ or $R_2$ is an alkyl group having from 1 to 10 carbon atoms.

Monomeric units of type represented by Formula I can be synthesized by techniques well known in the art. Specific methodologies for making preferred monomeric units are provided within the Example section below.

In some preferred embodiments, z is 1, and $R_1$ through $R_4$ are independently selected from alkyl groups, e.g. lower alkyl groups such as those having from 1 to 10 carbon atoms, e.g. methyl, ethyl, propyl, etc., and fluoro-substituted lower alkyl groups, as such monomeric units are significantly easiser to synthesize and analyze. Specific examples of preferred monomeric units include those represented by Formulae II and III:

$$\overset{O}{\underset{}{\parallel}}\diagup O \diagdown \diagup \diagdown \underset{|}{\overset{|}{Si}} \diagdown \underset{|}{\overset{O}{\underset{|}{Si}}} \diagdown \diagup \diagdown O \diagup \diagdown (CF_2)_4-H \quad (II)$$

$$\overset{O}{\underset{}{\parallel}}\diagup O \diagdown \diagup \diagdown \underset{|}{\overset{|}{Si}} \diagdown \underset{|}{\overset{O}{\underset{|}{Si}}} \diagdown \diagup \diagdown CF_3 \quad (III)$$

Applicable silicone-containing monomeric units for use in the formation of low water silicone compositons are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of applicable silicone-containing monomeric units include ethylenically "end-capped" siloxane-containing monomeric units used in the subject composition may be represented Formula IV:

$$A'-R'-\underset{R_9}{\overset{R_8}{Si}}-(-O-\underset{R_{11}}{\overset{R_{10}}{Si}})_a-(-O-\underset{R_{13}}{\overset{R_{12}}{Si}})_b-(-O-\underset{R_{15}}{\overset{R_{14}}{Si}})_c-O-\underset{R_{17}}{\overset{R_{16}}{Si}}-R''-A'' \quad (IV)$$

wherein:

A' and A" are activated unsaturated groups;

R' and R" independently are an alkyl or alkylene group having 1 to 10 carbon atoms wherein the carbon atoms may include ether linkages therebetween;

$R_8$ through $R_{17}$ are independently selected from monovalent hydrocarbon radicals or halogen substituted monovalent hydrocarbon radicals having 1 to 18 carbon atoms which may include ether linkages therebetween, but preferably are chosen from the groups described with reference to $R_1$ though $R_4$; a is an integer equal to or greater than 1; b and c are integers equal to or greater than 0; and a+b+c equals an integer from 1 to 1000.

Preferably, $R_8$ through $R_{17}$ are independently selected from alkyl groups and fluoro-substituted alkyl groups. It is further preferred that at least one of $R_8$ through $R_{17}$ includes a fluoro-substituted alkyl group such as that represented by the formula:

$$—D'—(CF_2)_s—M'$$

wherein:

D' is an alkyl or alkylene group having 1 to 10 carbon atoms wherein said carbon atoms may include ether linkages therebetween;

M' is hydrogen, fluorine, or alkyl group but preferably hydrogen or fluorine; and s is an integer from 1 to 20, preferably 1 to 6.

With respect to A, A', and A", the term "activated" is used to describe unsaturated groups which include at least one substituent which facilitates free radical polymerization. Preferably the activating groups facilitate polymerization under mild conditions, such as ambient temperatures. Although a wide variety of such groups may be used, preferably, A, A', and A" are esters or amides of an acrylic or methacrylic acid represented by the general formula:

<chemical structure> wherein X is preferably hydrogen or methyl but may include other groups, e.g. cyano, and Y is preferably —O—, —S—, or —NH—, but is more preferably —O—. Examples of other suitable groups include vinyl carbonates, vinyl carbamates, acrylonitryl, and styryl. Still another example of a suitable group includes N-vinyl-2-pyrrolidinone-(3,4, or 5)yl as shown in the following formula:

<chemical structure>

D, R, R', and R" represent divalent hydrocarbon radicals, preferably alkyl or alkylene groups having 1 to 10 and which may include ether linkages between carbon atoms. Preferably such alkyl or alkylene groups include 1 to 6 carbon atoms. Examples of such groups include methylene, propylene, butylene, pentamethylene, hexamethylene, etc., arylene radicals such as phenylene and biphenylene, and —O—$(CH_2)_q$—, wherein q is preferably 1 to 6.

Specific examples of preferred monomeric units include those represented by Formulae V and VI:

<chemical structure (V)>

<chemical structure (VI)> wherein:

d, e, f, and g, are integers from 0 to 1000, d+e equals an integer from 2 to 1000, preferably 2 to 100, f+g equals an integer from 2 to 1000, preferably 2 to 100, wherein e and g are preferably integers from about 20 to about 50, and h is an integer from 1 to about 20.

The synthesis of monomeric units as represented by Formula IV, V, VI, and similar monomeric units are well known in the art. Specific examples are provided in the Examples below.

Further examples of suitable silicone-containing monomers include bulky polysiloxanylalkyl (meth)acrylic monomers represented by Formula VII:

<chemical structure (VII)> wherein:

X denotes —O— or —NR—; each $R_{18}$ independently denotes hydrogen or methyl; each $R_{19}$ independently denotes a lower alkyl radical or a phenyl radical; and h is 1 to 10.

Such bulky monomers include methacryloxypropyl tris(trimethylsiloxy)silane.

Another preferred class of silicone containing monomers includes silicone-containing vinyl carbonate or vinyl carbamate monomers of Formula VIII:

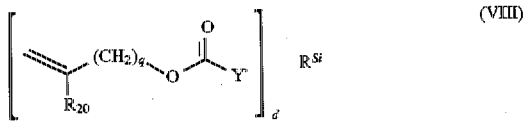

wherein:

Y' denotes —O—, —S— or —NH—;

$R^{Si}$ denotes a silicone-containing organic radical;

$R_{20}$ denotes hydrogen or methyl; d is 1, 2, 3 or 4; and q is 0 or 1.

Suitable silicone-containing organic radicals $R^{Si}$ include the following:

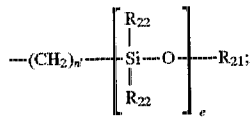

and

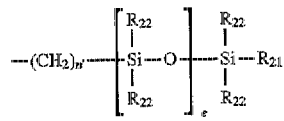

wherein:

$R_{21}$ denotes

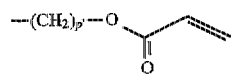

wherein p' is 1 to 6;

$R_{22}$ denotes an alkyl radical or a fluoroalkyl radical having 1 to 6 carbon atoms;

e is 1 to 200; n' is 1, 2, 3 or 4; and m' is 0, 1, 2, 3, 4 or 5.

The silicone-containing vinyl carbonate or vinyl carbamate monomers specifically include: 1,3-bis[4-vinyloxycarbonyloxy)but-1-yl]tetramethyl-disiloxane; 3-(trimethyl silyl) propyl vinyl carbonate; 3-(vinyloxycarbonylthio)propyl-[tris(trimethylsiloxy)silane]; 3-[tris (trimethylsiloxy)silyl] propyl vinyl carbamate; 3-[tris(trimethylsiloxy)silyl] propyl allyl carbamate; 3-[tris(trimethylsiloxy)silyl] propyl vinyl carbonate; t-butyldimethylsiloxyethyl vinyl carbonate; trimethylsilylethyl vinyl carbonate; trimethylsilylmethyl vinyl carbonate; and "$V_2D_{25}$", represented by Formula IX.

A further preferred class of silicone-containing monomers includes monomers of the Formulae X and XI:

or

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A denotes a divalent polymeric radical of Formula XII:

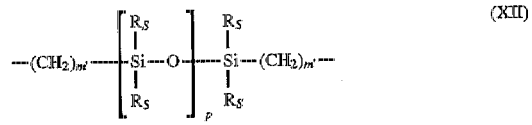

wherein:

each Rs independently denotes an alkyl or fluoro-substituted alkyl group having 1 to 10 carbon atoms which may contain ether linkages between carbon atoms;

m' is at least 1; and p is a number which provides a moiety weight of 400 to 10,000;

each of E and E' independently denotes a polymerizable unsaturated organic radical represented by Formula XIII:

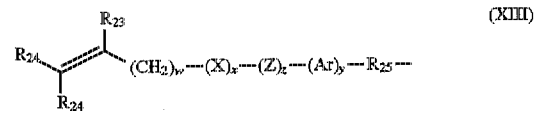

wherein:

$R_{23}$ is hydrogen or methyl;

$R_{24}$ is hydrogen, an alkyl radical having 1 to 6 carbon atoms, or a —CO—Y—$R_{26}$ radical wherein Y is —O—, —S— or —NH—;

$R_{25}$ is a divalent alkylene radical having 1 to 10 carbon atoms; $R_{26}$ is a alkyl radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred urethane monomer is represented by Formula (XIV):

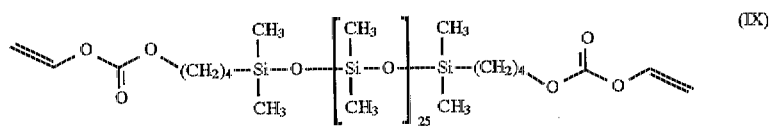

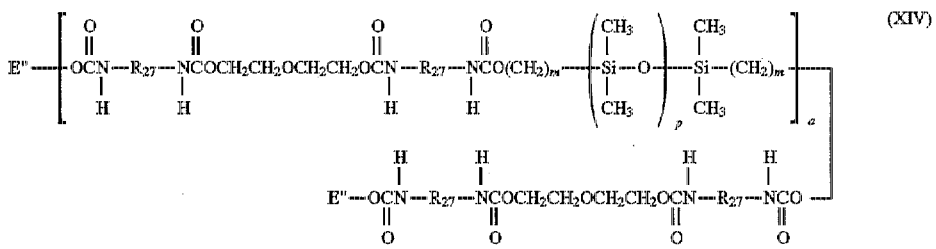
(XIV)

wherein m is at least 1 and is preferably 3 or 4, a is at least 1 and preferably is 1, p is a number which provides a moiety weight of 400 to 10,000 and is preferably at least 30, $R_{27}$ is a diradical of a diisocyanate after removal of the isocyanate group, such as the diradical of isophorone diisocyanate, and each E" is a group represented by:

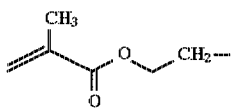

The monomer mix of the present invention may include additional constituents such as crosslinking agents, internal wetting agents, hydrophilic monomeric units, toughening agents, and other additives as is well known in the art.

Although the previously described ethylenically terminated siloxane-containing monomeric units form a crosslinked three-dimensional network when polymerized, additional crossing agents may be added to the monomer mix. Examples of suitable crosslinking agents include: polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N,N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, mannitol, and sorbitol. Further, illustrations include N,N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM) as disclosed in U.S. Pat. No. 4,954,587.

Other known crosslinking agents are polyether-bisurethane-dimethacrylates as described in U.S. Pat. No. 4,192,827, and those crosslinkers obtained by reaction of polyethylene glycol, polypropylene glycol and polytetramethylene glycol with 2-isocyanatoethyl methacrylate (IEM) or m-isopropenyl-γ,γ,-dimethylbenzyl isocyanates (m-TMI), and polysiloxane-bisurethane-dimethacrylates as described in U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

Although not required, compositions within the scope of the present invention may include toughening agents, preferably in quantities of less than about 80 weight percent, and more typically from about 20 to about 60 weight percent. Examples of suitable toughening agents are described in U.S. Pat. No. 4,327,203. These agents include cycloalkyl acrylates or methacrylate, such as: menthyl acrylate and methacrylate, tertiarybutylcyclohexyl methacrylate, isopropylcyclopentyl acrylate, tertiarypentylcyclo-heptyl methacrylate, tertiarybutylcyclohexyl acrylate, isohexylcyclopentyl acrylate and methylisopentyl cyclooctyl acrylate. Additional examples of suitable toughening agents are described in U.S. Pat. No. 4,355,147. This reference describes polycyclic acrylates or methacrylates such as: isobornyl acrylate and methacrylate, dicyclopentadienyl acrylate and methacrylate, adamantyl acrylate and methacrylate, and isopinocamphyl acrylate and methacrylate. Further examples of toughening agents are provided in U.S. Pat. No. 5,270,418. This reference describes branched alkyl hydroxyl cycloalkyl acrylates, methacrylates, acrylamides and methacrylamides. Representative examples include: 4-t-butyl, 2-hydroxycyclohexyl methacrylate (TBE);: 4-t-butyl, 2-hydroxycyclopentyl methacrylate; methacryloxyamino-4-t-butyl-2-hydroxycyclohexane; 6-isopentyl, 3-hydroxycyclohexyl methacrylate; and methacryloxyamino, 2-isohexyl, 5-hydroxycyclopentane.

Internal wetting agents are commonly used in low water formulations for increasing the wettability of such materials. Internal wetting agents typically do not account for more than 20 weight percent of the composition, and more commonly do not account for more than 10 weight percent, depending of course upon the specific wetting agent or combination of wetting agents used. In any event, the total water content of the resulting composition is less than about 5 weight percent water, and more commonly less than about 1 or 2 weight percent water. Examples of suitable internal wetting agents include N-alkyenoyl trialkylsilyl aminates as described in U.S. Pat. No. 4,652,622. These agents can be represented by the general formula:

wherein:

E is hydrogen or methyl,

G is $(CH_2)_rC(O)OSi(V)_3$ or hydrogen,

V is methyl, ethyl or propyl, q is an integer form 1 to 15, r is an integer form 1 to 10, q+r is an integer form 1 to 15, hereinafter referred to as NATA.

Acryloyl- and methacryloxy-, mono- and dicarboxylic amino acids, hereinafter NAA, impart desirable surface wetting characteristics to polysiloxane polymers, but precipitate out of siloxane monomer mixtures before polymerization is completed. NAA can be modified to form trialkylsilyl esters which are more readily incorporated into polysiloxane polymers. The preferred NATAs are trimethylsilyl-N-methacryloxyglutamate, triethylsilyl-N-methacryloxyglutamate, trimethyl-N-methacryloxy-6-aminohexanoate, trimethylsilyl-N-methacryloyl-aminododecanoate, and bis-trimethyl-silyl-N-methacryloxy aspartate.

Preferred wetting agents also include acrylic and methacrylic acids, and derivatives thereof. Typically, such wetting agents comprise less than 5 weight percent of the composition.

Other preferred internal wetting agents include oxazolones as described in U.S. Pat. No. 4,810,764 to Friends et al. issued Mar. 7, 1989. These materials can be represented by the formula:

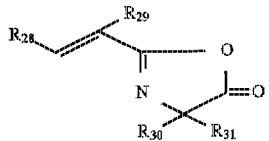

wherein:

$R_{28}$ and $R_{29}$ are independently selected from hydrogen or methyl, and $R_{30}$ and $R_{31}$ are independently selected from methyl of cyclohexyl radicals.

These preferred internal wetting agents specifically include 2-isopropenyl-4,4-dimethyl-2-oxazolin-5-one (IPDMO), 2-vinyl-4,4-dimethyl-2-oxazolin-5-one (VDMO), cyclohexane spiro-4'-(2'isopropenyl-2'-oxazol-5'-one) (IPCO), cyclohexane-spiro-4'-(2'-vinyl-2'-oxazol-5'-one) (VCO), and 2-(-1-propenyl)-4,4-dimethyl-oxazol-5-one (PDMO). The preparation of such oxazolones is known in the art and is described in U.S. Pat. No. 4,810,764.

These preferred internal wetting agents have two important features which make them particularly desirable wetting agents: (1) they are relatively non-polar and are compatible with the hydrophobic monomers (the polysiloxanes and the toughening agents), and (2) they are convened to highly polar amino acids on mild hydrolysis, which impart substantial wetting characteristics. When polymerized in the presence of the other components, a copolymer is formed. These internal wetting agents polymerize through the carbon-carbon double bond with the endcaps of the polysiloxane monomers, and with the toughening agents to form copolymeric materials particularly useful in biomedical devices, especially contact lenses.

Further examples of internal wetting agents include hydrophilic monomeric units such as those described in U.S. Pat. Nos. 4,259,467; 4,260,725; 4,440,918; 4,910,277; 4,954,587; 4,990,582; 5,010,141; 5,079,319; 5,310,779; 5,321,108; 5,358,995; 5,387,662; all of which are incorporated herein by reference. Examples of such hydrophilic monomers include both acrylic- and vinyl-containing monomers.

Preferred hydrophilic monomers may be either acrylic- or vinyl-containing. Such hydrophilic monomers may themselves be used as crosslinking agents. The term "vinyl-type" or "vinyl-containing" monomers refers to monomers containing the vinyl grouping ($CH_2$=CQH), and are generally highly reactive. Such hydrophilic vinyl-containing monomers are known to polymerize relatively easily. "Acrylic-type" or "acrylic-containing" monomers are those monomers containing the acrylic group represented by the formula:

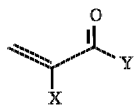

wherein X is preferably hydrogen or methyl and Y is preferably —O—, —OQ—, —NH—, —NQ— and —NH (Q)—, wherein Q is typically an alkyl or substituted alkyl group. Such monomers are known to polymerize readily.

Preferred hydrophilic vinyl-containing monomers which may be incorporated into the low water compositions of the present invention include monomers such as N-vinyl lactams (e.g. N-vinyl pyrrolidone (NVP)), N-vinyl-N-methyl acetamide, N-vinyl-N- ethyl acetamide, N-vinyl-N-ethyl formamide, N-vinyl formamide, with NVP being the most preferred.

Preferred hydrophilic acrylic-containing monomers which may be incorporated into the hydrogel of the present invention include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, with DMA being the most preferred.

When both an acrylic-containing monomer and a vinyl-containing monomer are incorporated into the invention, a further crosslinking agent having both a vinyl and an acrylic polymerizable group may be used, such as the crosslinkers which are the subject of U.S. Pat. No. 5,310,779, issued May 10, 1994, the entire content of which is incorporated by reference herein. Such crosslinkers help to render the resulting copolymer totally UV-curable. However, the copolymer could also be cured solely by heating, or with a combined UV and heat regimen. Photo and/or thermal initiators required to cure the copolymer will be included in the monomer mix, as is well-known to those skilled in the art. Other crosslinking agents which may be incorporated into the silicone-containing hydrogel including those previously described.

Other techniques for increasing the wettability of compositions may also be used within the scope of the present invention, e.g. plasma surface treatment techniques as is well known in the art.

Particularly preferred low water compositions comprise from 5 to 40 weight percent of monomeric units represented by Formula I, from 30 to 60 weight percent of the monomeric unit represented by Formula IV, and from 15 to 40 weight percent of a toughening agent. Such formulations may also include additional constituents such as octafluoropentylmethacrylate, (OFPMA). Such monomeric units may be synthesized using techniques known in the art. Related materials are described in U.S. Pat. No. 4,810,764 which is incorporated herein by reference.

The monomer mixes employed in this invention, can be readily cured to cast shapes by conventional methods such as UV polymerization, or thermal polymerization, or combinations thereof, as commonly used in polymerizing ethylenically unsaturated compounds. Representative free radical thermal polymerization initiators are organic peroxides, such as acetal peroxide, lauroyl peroxide, decanoyl peroxide, stearoyl peroxide, benzoyl peroxide, tertiarybutyl peroxypivalate, peroxydicarbonate, and the like, employed in a concentration of about 0.01 to 1 percent by weight of the total monomer mixture. Representative UV initiators are those known in the field such as, benzoin methyl ether, benzoin ethyl ether, Darocure 1173, 1164, 2273, 1116, 2959, 3331 (EM Industries) and Igracure 651 and 184 (Ciba-Geigy).

Polymerization of the monomeric units of this invention with other comonomers is generally performed (with crosslinking agents) in the presence of a diluent. The polymerization product will typically be in the form of a gel. If the diluent is nonaqueous, the diluent must be removed from the gel and replaced with water through the use of extraction and hydration protocols well known to those skilled in the art.

In addition to the above-mentioned polymerization initiators, the copolymer of the present invention may also include other monomers as will be apparent to one skilled in the art. For example, the monomer mix may include colorants, or UV-absorbing agents such as those known in the contact lens art.

The present invention provides materials which can be usefully employed for the fabrication of prostheses such as heart valves and intraocular lenses, films, surgical devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices, and especially contact lenses.

The polymers of this invention can be formed into contact lenses by spincasting processes (such as those disclosed in U.S. Pat. Nos. 3,408,429 and 3,496,254), cast molding, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

When used in the formation of contact lenses, it is preferred that the subject hydrogels have water contents of less than about 5 weight percent and more preferably less than about 1 weight percent. Furthermore, it is preferred that such hydrogels have a modulus from about 20 g/mm$^2$ to about 150 g/mm$^2$, and more preferably from about 30 g/mm$^2$ to about 100 g/mm$^2$.

As an illustration of the present invention, several examples are provided below. These examples serve only to further illustrate aspects of the invention and should not be construed as limiting the invention.

EXAMPLE I

Ten low water polysiloxane compositions were prepared, each consisting of various amounts of three primary constituents: the ethylenically terminated siloxane containing monomeric units represented by Formula V, the monomeric units represented by Formula II, and octafluoropentylmethacrylate, hereinafter referred to below as OFPMA.

The monomeric unit represented by Formula V, i.e. poly (65 mole % trifluoropropylmethylsiloxane)-co-(35 mole % dimethylsiloxane), referred to as "65-TFP," was prepared as follows.

Octamethylcydotetrasiloxane (39.4 g, 0.133 mole) trifluoropropylcyclotrisiloxane (154.3 g, 0.33 mole) and methacryloxybutyltetramethyldisiloxane (6.3 g, 0.015 mole) were added at room temperature to a round bottom flask under dry nitrogen. Trifluoromethanesulfonic acid (0.54 g, 3.6 mmole) was added and the reaction mixture was stirred for 24 hours. Sodium bicarbonate was then added to the viscous reaction product and the stirring continued for 16 hours. Following the neutralization procedure, chloroform (500 mls) was added and the solution was dried over magnesium sulfate and filtered using a 5μ millipore Teflon filter. The filtrate was placed on a rotary evaporator and the chloroform was removed. The resultant prepolymer was added dropwise with rapid stirring to 500 ml of methanol to remove the unreacted cyclics. The polymer layer was collected and the procedure was repeated twice. Following the third fractionation, the polymer was collected, dissolved in diethylether, dried over magnesium sulfate and again filtered through a 5μ filter. The filtered solution was placed on the rotary evaporator and the diethylether was removed. The resultant clear fluid was vacuum stripped at 80° C. for 4 hours (at 0.2 mm Hg) to remove low molecular weight cyclics. The molecular structure of the purified 65-TFP (150 g, 75%) was confirmed by NMR spectroscopy.

The monomeric units represented by Formula II, i.e. 1-(methacryloxypropyl)-3-(3-(2,2,3,3,4,4,5,5-octafluoropentoxy)-propyl)tetramethyldisiloxane, referred to below as "MO," was prepared as follows.

(a) Preparation of trimethylsilyl protected hydroxypropyl tetramethyldisiloxane

To a 1 L round bottom flask is added 1,3-tetramethyldisiloxane (100 g, 0.774 mole), allyloxytrimethylsilane (97.0 g, 0.779 mole), 0.008 g of a (TRIS (triphenylphosphine) rhodium) chloride and 400 mls of toluene. The solution is heated to 80° C. for two hours at which time the silicone hydride is reacted as shown by $^1$H-NMR spectroscopy. The toluene is removed using a rotoevaporator and the resultant oil is vacuum distilled (65° C./1.5 mmHg) to yield 127.5 g (64.8% yield) of trimethylsilyl protected hydroxy propyl tetramethyldisiloxane.

(b) Preparation of 1-(3-trimethylsilyloxypropyl)-3-(3-(2,2,3,3,4,4,5,5-octafluoropentoxy)-propyl) tetramethyldisiloxane To a 1 L round bottom flask is added trimethylsilyl protected hydroxy propyl tetramethyldisiloxane (60 g, 0.227 mole), allyloxyoctafluoropentane (74.1 g, 0.272 mole), platinum divinyl tetramethyldisiloxane complex (113 ul, 0.002 mole/ul catalyst), 200 mls of THF and 200 mls of 1,4-dioxane. The solution is heated to 80° C. for three hours at which time the solvent is removed using a rotoevaporator. The resultant oil is passed through 50 g of silica gel using a 10/1 mixture of pentane and methylene chloride. The solvent is removed using a rotoevaporator and the resultant oil is vacuum distilled (120° C./0.2mmHg) to yield 103 grams of a 97% pure 1-(3-trimethylsilyloxypropyl)-3-(3-(2,2,3,3,4,4,5,5-octafluoropentoxy-propyl) tetramethyldisiloxane.

(c) Preparation of 1-(methacryloxypropyl)-3-(3-(2,2,3,3,4,4,5,5-octafluoropentoxy)-propyl) tetramethyldisiloxane 1-(3-trimethylsilyloxypropyl)-3-(3-(2,2,3,3,4,4,5,5-octafluoro-pentoxy propyl) tetra-methyldisiloxane (53.7 g, 0.01 mole) is dissolved in 540 ml of methanol. To this solution is added 8.8 ml of a 10% solution of acetic acid at room temperature. The mixture is stirred for one hour and the solvent is removed on a rotoevaporator at 40° C. The resultant oil is dissolved in 300 mls of hexane and washed four times with distilled water. The organic layer is collected, dried over magnesium sulfate and filtered.

The filtered reaction product from above, (1-(3-hydroxypropyl)-3-(3-(2,2,3,3,4,4,5,5-octafluoropentoxypropyl)-tetramethyldisiloxane), (46.3 g, 0.1 mole), is added to a 1 L round bottom flask along with triethylamine (11.1 g, 0.110 mole). The solution is cooled to 0° C. and methacryloxy chloride (11.5 g, 0.11 mole) is slowly added. Following the addition of methacryloxy chloride, the solution is brought to room temperature and allowed to stir overnight. The next day the resultant solution is extracted two times with 1N HCl, two times with 2N NaOH and two times with distilled water. The organic layer is collected and dried over magnesium sulfate. The solution is filtered and the solvent is removed using a rotoevaporator. The resultant oil is passed through 50 g of silica gel using a 10/1 mixture of pentane and methylene chloride. The solvent is removed using a rotoevaporator and the resultant oil is vacuum distilled (120° C./0.1 mmHg) to yield 34.1 grams (64% yield) of a 95% pure 1-(3-methacryloxypropyl)-3-(3-(2,2,3,3,4,4,5,5-octafluoro-pentoxy propyl) tetramethyldisiloxane monofork.

An overview of this synthesis is represented by the following reaction pathway:

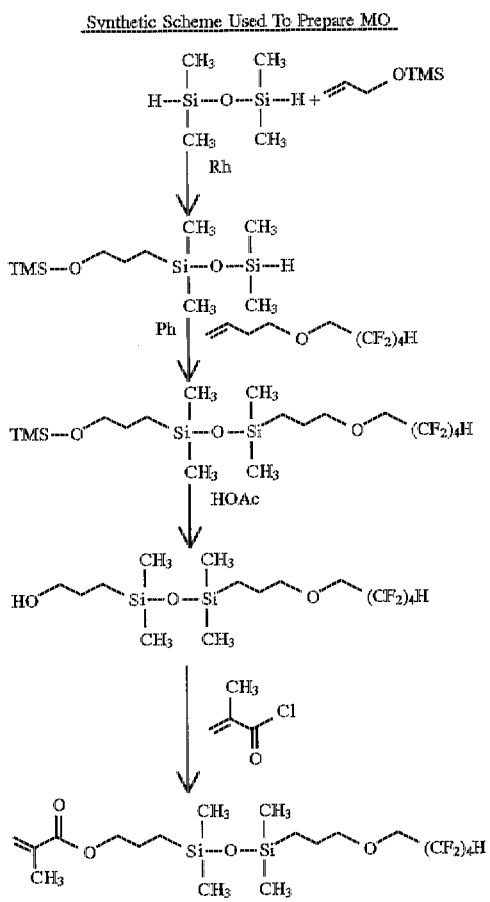

The specific ratios of 65TFP, MO, and OFPMA for the ten compositions are provided in Table I below.

Each of the constitituents of each sample were combined in the ratios indicated in Table I along with a UV initiator and mixed for approximately 20 minutes. Each of the ten compositions were then cast as a film for mechanical property evaluations using the following procedure. Films of each composition were cast between silanized glass plates with a 0.3 mm Teflon spacer using cure conditions of 2 hours of UV at an intensity of 3500 μW/cm². The UV initiator was Darocur 1173 (0.5% concentration). The resultant films were extracted 16 hours in 2-propanol and two hours in distilled water followed by a 16 hour hydration in phosphate-buffered saline (pH 7.3). The mechanical properties of films were determined on an Instron Model 4500 using ASTM methods 1708 and 1938. Oxygen permeability (DK) was determined using the polarographic probe method (I. Fatt, I. E. Rasson, and J. B. Melpolder, *ICLC J.*, 14, 38 (1987). The hydrolyric stability test consisted of heating the test films in phosphate-buffered saline for 3, 5, 7, and 14 days at 80° C. and monitoring the change in weight and water content. The results of mechanical properties evaluation for each sample composition are provided in Table I.

TABLE I

| Composition (Wt. %) 65TFP/MO/OFPMA | Young's Modulus (g/mm²) | Tear Strength (g/mm) | Oxygen Permeability (barrers) |
|---|---|---|---|
| 80/0/20 | 110 | 5 | 360 |
| 75/5/20 | 79 | 3 | 275 |
| 70/10/20 | 74 | 3 | 240 |
| 60/20/20 | 58 | 2 | 220 |
| 60/0/40 | 351 | 29 | 213 |
| 55/5/40 | 188 | 29 | 190 |
| 50/10/40 | 121 | 36 | NA |
| 45/15/40 | 68 | 24 | 155 |
| 40/20/40 | 73 | 26 | NA |
| 30/30/40 | 44 | 29 | 145 |

EXAMPLE II

Example II consisted of three low water polysiloxane compositions prepared and evaluated in substantially the same manner as described with respect to Example I, with the exception that monomeric units represented by Formula III were substituted for those represented by Formula II. That is, 1-(methyacryolyoxypropyl)-3-(trifluoropropyl) tetramethyldisiloxane) (MTFP) was substituted for MO. The specific ratios of each constituent along with mechanical property evaluations are provided in Table II.

TABLE II

| Composition (Wt. %) 65TFP/MTFP/OFPMA | Young's Modulus (g/mm²) | Tear Strength (g/mm) | Oxygen Permeability (barrers) |
|---|---|---|---|
| 60/0/40 | 351 | 29 | 213 |
| 50/10/40 | 189 | 58 | 178 |
| 40/20/40 | 89 | 40 | 148 |

Tables I and II show the modulus, tear strength, and oxygen permeability data for films cast from the 65TFP/MO/OFPMA, and the 65TFP/MTFP/OFPMA formulations. As is clear from the data provided, the subject monomeric units, i.e. MO and MTFP (represented by Formulae II and III, respectively), significantly reduced the modulus in both low water formulations.

EXAMPLE III

Lenses were cast between polypropylene anterior and posterior molds using the 65TFP/MO/OFPMA (45/15/40) formulations with 0.5% Darocur 1173 as UV initiator using the cure conditions listed above. Following cure, the lenses were released in toluene and extracted overnight in toluene at room temperature. The lenses were plasma treated using conventional air plasma techniques resulting in contact lenses that possessed excellent wetting characteristics.

EXAMPLE IV

Although the synthesis of monomeric units represented by Formula I are known in the art, an additional representative synthesis is provided. More specifically, the preparation of Methacrylpropyl di(octafluoropentyloxypropyldimethylsilyl-oxy) methylsilane is provided below.

(a) Preparation of Methacryloxypropyl methyl di-(methylsiloxy)silane

To a three neck round bottom flask equipped with a thermometer and magnetic stirrer is added methacryloxypropyldichloromethylsilane (25 g 0.104 mole), dimethylchlorosilane (39.2, 0.415 mole), triethylamine (45.5, 0.450 mole) and 250 ml of anhydrous diethylether. The reaction mixture is cooled to −15° C. and distilled water (14.9, 0.830 mole) is slowly added. The reaction is allowed to come to room temperature slowly and the reaction is stirred overnight. The resultant solution is washed three times with distilled water. The ether layer is collected, dried over magnesium sulfate, filtered and the diethyl ether is removed using a rotoevaporator. The resultant oil is vacuum distilled (105° C./0.15 mm) to give a 50% yield of 94% pure (as determined by GC) methacryloxypropyl tris (dimethysilyloxy) silane.

(b) Preparation of Methacrylpropyl di(octafluoropentyloxypropyldimethylsilyloxy) methylsilane To a 200 ml round bottom flask is added methacryloxypropyl tris (dimethylsilyloxy)silane (8.0 g, 0.0249 mole), allyloxyoctafluoropentane (15 g, 0.055 mole), 0.030 ml of a platinum divinyl complex (huels) and 80 mls of tetrahydrofuran. The solution is refluxed for one hour at which time the silicone hydride is reacted as shown by $^1$H-NMR spectroscopy. The THF and unreacted allyloxyoctafluoropentane is removed using a rotoevaporator (50° C./30 mm) resulting in a quantitative yield of methacrylpropyl di(octafluoropentyloxypropyldimethylsilyloxy) methylsilane Many other modifications and variations of the present invention are possible to the skilled practitioner in the field in light of the teachings herein. It is therefore understood that, within the scope of the claims, the present invention can be practiced other than as herein specifically described.

We claim:

1. A low water polymeric silicone composition having a Young's modulus of elasticity from about 20 g/mm$^2$ to about 150 g/mm$^2$ and formed by polymerizing a monomer mix comprising monomeric units represented by Formula I:

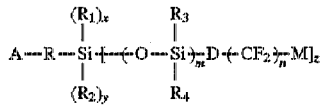

wherein:

A is an activated unsaturated group;

R and D independently are alkyl, alkylene, or haloalkyl groups having 1 to 10 carbon atoms wherein said carbon atoms may include ether linkages therebetween;

M is hydrogen, fluorine, or an alkyl group;

$R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;

m is an integer from 1 to 500; n is an integer from 1 to 20; x and y are 0 or 1;

z is 1 or 2; and x+y+z=3;

so long as at least one of $R_1$ or $R_2$ is an alkyl group having from 1 to 10 carbon atoms.

2. The composition of claim 1 wherein z is 1; $R_1$, $R_2$, $R_3$, and $R_4$ are independently selected from alkyl groups having from 1 to 10 carbon atoms; A is a group selected from: an ester or amide of acrylic acid or methacrylic acid; R and D are alkyl groups having firm 1 to 6 carbon atoms wherein said carbon atoms may include ether linkages therebetween; m is from 1 to 10; and n is from 1 to 6.

3. The composition of claim 1 wherein the monomeric units represented by Formula I include monomeric units represented by at least one of Formulae II and III:

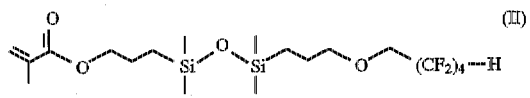

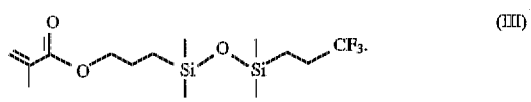

4. The composition of claim 1 formed by polymerizing comprising the following:

(a) from about 1 to about 99 weight percent of silicone-containing monomeric units other than those represented by Formula I; and (b) from about 1 to about 50 weight percent of the monomeric units represented by Formula I.

5. The composition of claim 4 wherein said silicone-containing monomeric units comprise monomeric units represented by Formula IV:

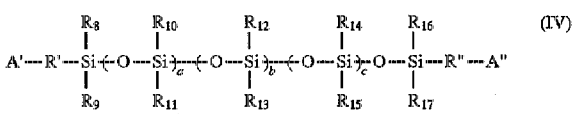

wherein:

A' and A" are activated unsaturated groups;

R' and R" independently are an alkyl or alkylene group having 1 to 10 carbon atoms wherein the carbon atoms may include ether linkages therebetween;

$R_8$ through $R_{17}$ are independently selected from the groups described with reference to $R_1$ though $R_4$;

a is an integer equal to or greater than 1;

b and c are integers equal to or greater than 0; and a+b+c equals an integer from 1 to 1000.

6. The composition of claim 5 wherein A' and A" are groups selected from: an ester or amide of acrylic acid or methacrylic acid; R' and R" are selected from are alkyl groups having from 1 to 6 carbon atoms wherein said carbon atoms may include ether linkages therebetween; $R_8$ through $R_{17}$ are independently selected from alkyl groups having from 1 to 10 carbon atoms, and at least one of $R_8$ through $R_{17}$ is a fluoroosubstituted alkyl group.

7. The composition of claim 5 wherein said monomeric units represented by Formula IV include monomeric units selected from those represented by Formulae V and VI, and combinations thereof:

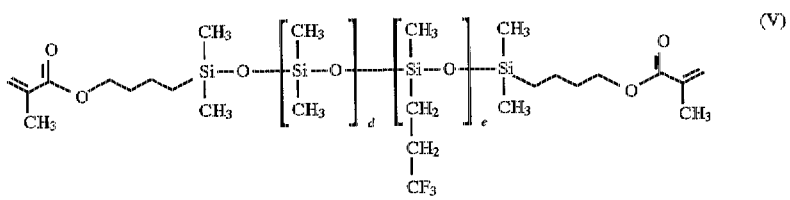

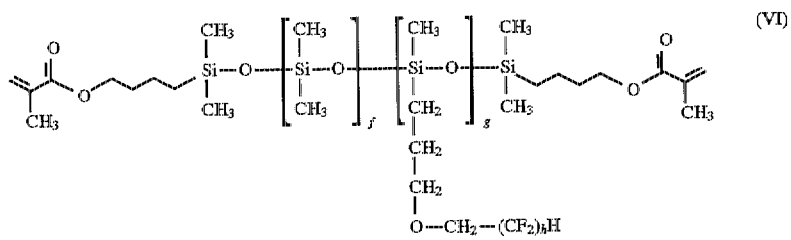

wherein:

d, e, f, and g, are integers from 0 to 1000;

d+e equals an integer from 2 to 1000;

f+g equals an integer from 2 to 1000; and h is an integer from 1 to about 20.

8. A contact lens comprising a low water polymeric silicone composition having a Young's modulus of elasticity from about 20 g/mm² to about 150 g/mm² and formed by polymerizing a monomer mix comprising monomeric units represented by Formula I:

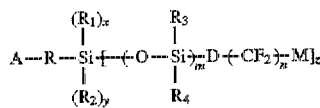

wherein:

A is an activated unsaturated group;

R and D independently are alkyl, alkylene, or haloalkyl groups having 1 to 10 carbon atoms wherein said carbon atoms may include ether linkages therebetween;

M is hydrogen, fluorine, or an alkyl group;

$R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;

m is an integer from 1 to 500; n is an integer from 1 to 20;

x and y are 0 or 1;

z is 1 or 2; and x+y+z=3;

so long as at least one of $R_1$ or $R_2$ is an alkyl group having from 1 to 10 carbon atoms.

9. The contact lens of claim 8 wherein z is 1; $R_1$, $R_2$, $R_3$, and $R_4$ are independently selected from alkyl groups having from 1 to 10 carbon atoms; A is a group selected from: an ester or amide of acrylic acid or methacrylic acid; R and D are alkyl groups having from 1 to 6 carbon atoms wherein said carbon atoms may include ether linkages therebetween; m is from 1 to 10; and n is from 1 to 6.

10. The contact lens of claim 8 wherein the monomeric units represented by Formula I include monomeric units represented by at least one of Formulae II and III:

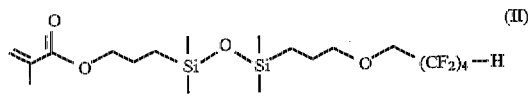

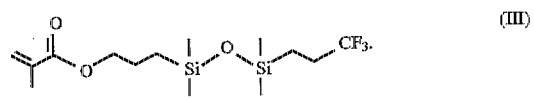

11. The contact lens of claim 8 wherein said composition is polymerized from a monomer mix comprising:

(a) from about 1 to about 99 weight percent of silicone-containing monomeric units other than those represented by Formula I; and (b) from about 1 to about 50 weight percent of the monomeric units represented by Formula I.

12. The contact lens of claim 11 wherein said silicone-containing monomeric units comprise monomeric units represented by Formula IV:

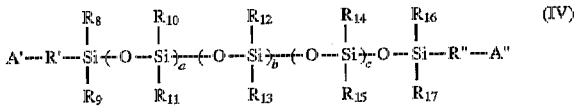

wherein:

A' and A" are activated unsaturated groups;

R' and R" independently are an alkyl or alkylene group having 1 to 10 carbon atoms wherein the carbon atoms may include ether linkages therebetween;

$R_8$ through $R_{17}$ are independently selected from the groups described with reference to $R_1$ though $R_4$;

a is an integer equal to or greater than 1;

b and c are integers equal to or greater than 0; and a+b+c equals an integer from 1 to 1000.

13. The contact lens of claim 12 wherein A' and A" are groups selected from: an ester or amide of acrylic acid or methacrylic acid; R' and R" are selected from are alkyl groups having from 1 to 6 carbon atoms wherein said carbon atoms may include ether linkages therebetween; $R_8$ through $R_{17}$ are independently selected from alkyl groups having from 1 to 10 carbon atoms, and at least one of $R_8$ through $R_{17}$ is a fluoro-substituted alkyl group.

14. The contact lens of claim 12 wherein said monomeric units represented by Formula IV include monomeric units selected from those represented by Formulae V and VI, and combinations thereof:

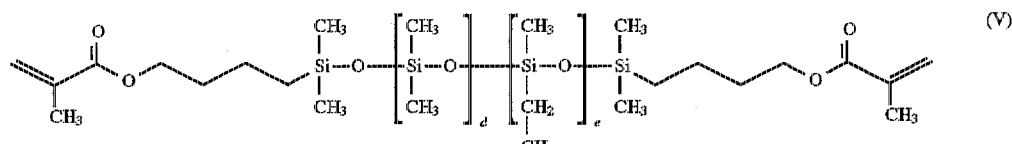

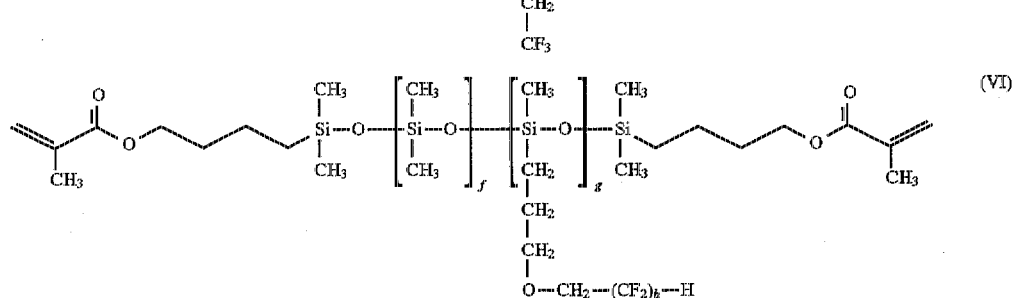

wherein:

d, e, f, and g, are integers from 0 to 1000;

d+e equals an integer from 2 to 1000;

f+g equals an integer from 2 to 1000; and h is an integer from 1 to about 20.

15. A method for making a low water polymeric silicone composition including the step of polymerizing a monomer mix comprising monomeric units represented by Formula I:

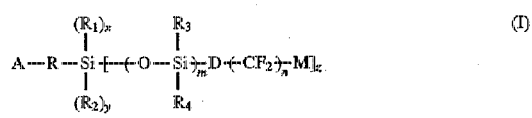

wherein:

A is an activated unsaturated group;

R and D independently are alkyl, alkylene, or haloalkyl groups having 1 to 10 carbon atoms wherein said carbon atoms may include ether linkages therebetween;

M is hydrogen, fluorine, or an alkyl group;

$R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;

m is an integer from 1 to 500; n is an integer from 1 to 20; x and y are 0 or 1;

z is 1 or 2; and x+y+z=3;

so long as at least one of $R_1$ or $R_2$ is an alkyl group having from 1 to 10 carbon atoms.

16. The method of claim 15 wherein z is 1; $R_1$, $R_2$, $R_3$, and $R_4$ are independently selected from alkyl groups having from 1 to 10 carbon atoms; A is a group selected from: an ester or amide of acrylic acid or methacrylic acid; R and D are alkyl groups having from 1 to 6 carbon atoms wherein said carbon atoms may include ether linkages therebetween; m is from 1 to 10; and n is from 1 to 6.

17. The method of claim 15 wherein the step of polymerizing a monomer mix is further characterized by preparing a monomer mix comprising:

(a) from about 1 to about 99 weight percent of silicone-containing monomeric units other than those represented by Formula I; and (b) from about 1 to about 50 weight percent of the monomeric units represented by Formula I.

18. The method of claim 17 wherein said silicone-containing monomeric units comprise monomeric units represented by Formula IV:

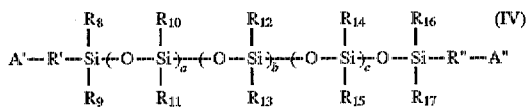

wherein:

A' and A" are activated unsaturated groups;

R' and R" independently are an alkyl or alkylene group having 1 to 10 carbon atoms wherein the carbon atoms may include ether linkages therebetween;

$R_8$ through $R_{17}$ are independently selected from the groups described with reference to $R_1$ though $R_4$;

a is an integer equal to or greater than 1;

b and c are integers equal to or greater than 0; and a+b+c equals an integer from 1 to 1000.

19. The method of claim 18 wherein A' and A" are groups selected from: an ester or amide of acrylic acid or methacrylic acid; R' and R" are selected from are alkyl groups having from 1 to 6 carbon atoms wherein said carbon atoms may include ether linkages therebetween; and $R_8$ through $R_{17}$ are independently selected from alkyl groups having from 1 to 10 carbon atoms.

* * * * *

UNITED STATES PATENT AND TRADEMARK OFFICE
CERTIFICATE OF CORRECTION

PATENT NO. : 5,714,557
DATED : February 3, 1998
INVENTOR(S) : Jay F. Kunzler and Richard M. Ozark It is certified that error appears in the above-identified patent and that said Letters Patent is hereby corrected as shown below:

In Column 18, lines 20-21, after "polymerizing", insert -- a monomer mix -- .

Signed and Sealed this

Thirty-first Day of March, 1998

Attest:

BRUCE LEHMAN

Attesting Officer

Commissioner of Patents and Trademarks